(12) United States Patent
Aizawa et al.

(10) Patent No.: US 10,132,812 B2
(45) Date of Patent: Nov. 20, 2018

(54) PRE-TREATMENT AGENT AND PRE-TREATMENT METHOD FOR ANTITHROMBIN III TO BE SUBJECTED TO LIMULUS TEST

(71) Applicant: SEIKAGAKU CORPORATION, Tokyo (JP)

(72) Inventors: Maki Aizawa, Tokyo (JP); Toshio Oda, Tokyo (JP); Jun Aketagawa, Tokyo (JP)

(73) Assignee: SEIKAGAKU CORPORATION, Chiyoda-ku, Tokyo (JP)

( * ) Notice: Subject to any disclaimer, the term of this patent is extended or adjusted under 35 U.S.C. 154(b) by 0 days.

(21) Appl. No.: 14/758,269

(22) PCT Filed: Dec. 27, 2013

(86) PCT No.: PCT/JP2013/085234
§ 371 (c)(1),
(2) Date: Jun. 29, 2015

(87) PCT Pub. No.: WO2014/104352
PCT Pub. Date: Jul. 3, 2014

(65) Prior Publication Data
US 2016/0061838 A1    Mar. 3, 2016

(30) Foreign Application Priority Data

Dec. 28, 2012   (JP) ................................ 2012-287475

(51) Int. Cl.
| | |
|---|---|
| *G01N 33/579* | (2006.01) |
| *C07K 14/81* | (2006.01) |
| *C07K 5/103* | (2006.01) |
| *C01F 5/30* | (2006.01) |
| *C01F 5/40* | (2006.01) |
| *C01F 11/24* | (2006.01) |
| *C01G 9/06* | (2006.01) |
| *C01G 45/10* | (2006.01) |

(52) U.S. Cl.
CPC .............. *G01N 33/579* (2013.01); *C01F 5/30* (2013.01); *C01F 5/40* (2013.01); *C01F 11/24* (2013.01); *C01G 9/06* (2013.01); *C01G 45/10* (2013.01); *C07K 5/101* (2013.01); *C07K 14/8128* (2013.01); *G01N 2333/8128* (2013.01)

(58) Field of Classification Search
CPC .......... G01N 33/579; G01N 2333/8128; C07K 14/8128
USPC ...................... 435/7.2; 252/183.14
See application file for complete search history.

(56) References Cited

U.S. PATENT DOCUMENTS

| | | | | |
|---|---|---|---|---|
| 4,495,294 | A * | 1/1985 | Nakahara ............. | G01N 33/579 435/18 |
| 5,286,625 | A | 2/1994 | Tanaka et al. | |
| 5,378,610 | A * | 1/1995 | Tanaka ................. | G01N 33/579 435/18 |
| 5,389,547 | A | 2/1995 | Tanaka et al. | |
| 5,476,772 | A * | 12/1995 | Tsuchiya .............. | G01N 33/579 435/18 |
| 5,550,030 | A | 8/1996 | Tanaka et al. | |
| 5,695,948 | A | 12/1997 | Tanaka et al. | |
| 7,867,722 | B2 * | 1/2011 | Oda ..................... | G01N 33/579 252/183.14 |
| 2009/0011448 | A1 | 1/2009 | Oda et al. | |

FOREIGN PATENT DOCUMENTS

| | | |
|---|---|---|
| EP | 0569033 A2 | 11/1993 |
| EP | 0844254 A2 | 5/1998 |
| JP | 4-102064 A | 4/1992 |
| JP | 6-70796 A | 3/1994 |
| JP | 6-130064 A | 5/1994 |
| JP | 9-178753 A | 7/1997 |
| JP | 2004-109147 A | 4/2004 |
| JP | 2005-308574 A | 11/2005 |
| JP | 2010-243342 A | 10/2010 |
| WO | 2006/080448 A1 | 8/2006 |

OTHER PUBLICATIONS

Sas et al. Investigations on Antithrombin III in Normal Plasma and Serum; British Journal of Haematology, vol. 30 (1975) pp. 265-272.*
International Search Report of PCT/JP2013/085234, dated Apr. 1, 2014.
Haruhiko Takada, et al., "New Development in Natural Immunity Research", Endotoxin Research 12, 2009, pp. 93-97.
Hiroko Tsutsui, et al., "Rapidly Developing Natural Immunity Research", Endotoxin and Natural Immunity Research 15, 2012, pp. 27-30.
Written Opinion of PCT/JP2013/085234, dated Apr. 1, 2014.
Communication for European Patent Application No. 13868898.1 dated Jul. 18, 2016, with Supplementary European Search Report (dated Jul. 11, 2016).
Communication dated Mar. 27, 2017, issued from the State Intellectual Property Office of People's Republic of China in corresponding Chinese Application No. 201380068652.2.
Communication dated May 5, 2016, from the State Intellectual Property Office of People's Republic of China in counterpart Application No. 201380068652.2.

* cited by examiner

*Primary Examiner* — Scott Long
*Assistant Examiner* — Paul C Martin
(74) *Attorney, Agent, or Firm* — Sughrue Mion, PLLC

(57) ABSTRACT

To provide means for reducing reaction interference observed when AT III is subjected to *limulus* test, whereby the *limulus* test of antithrombin III can be carried out at high accuracy. Reaction interference observed when AT III is subjected to *limulus* test can be reduced by subjecting AT III to a protein inactivation treatment in the co-presence of a divalent metal salt.

6 Claims, 2 Drawing Sheets

Specification includes a Sequence Listing.

[Fig. 1]
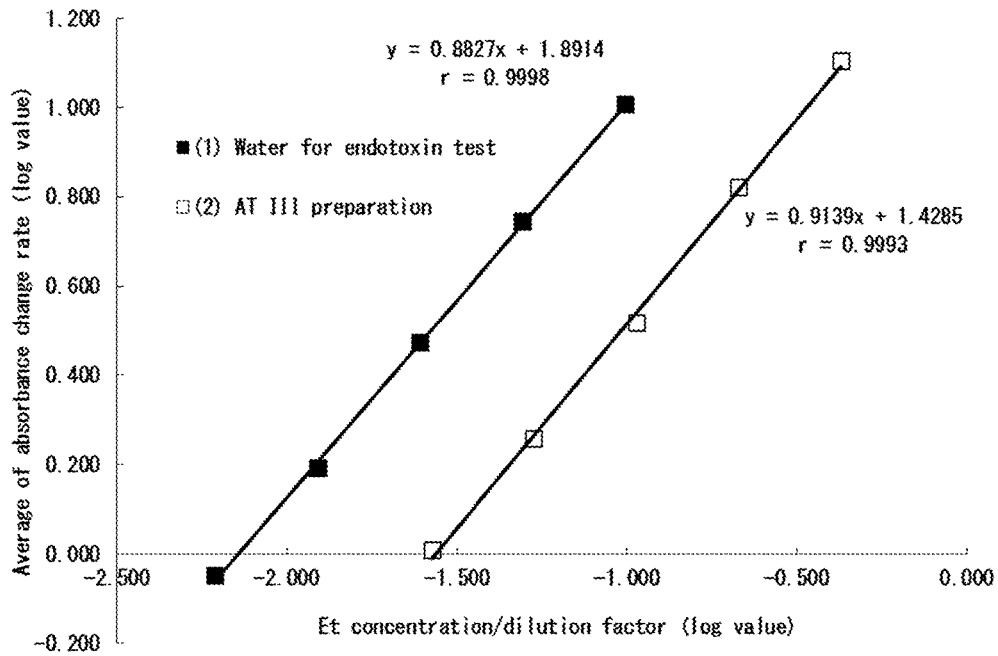
[Fig. 2]
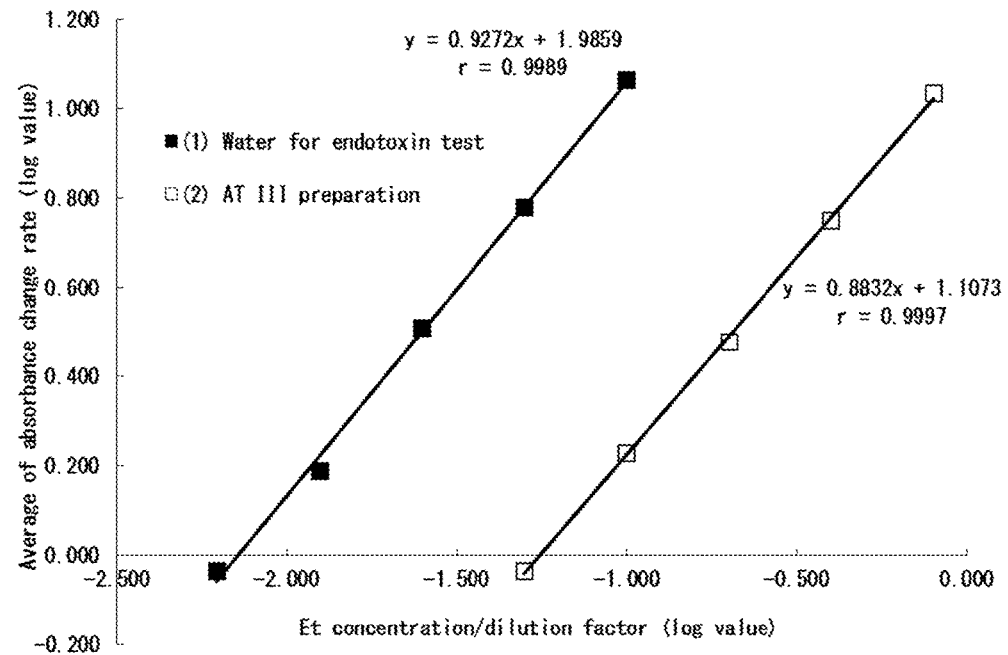

[Fig. 3]
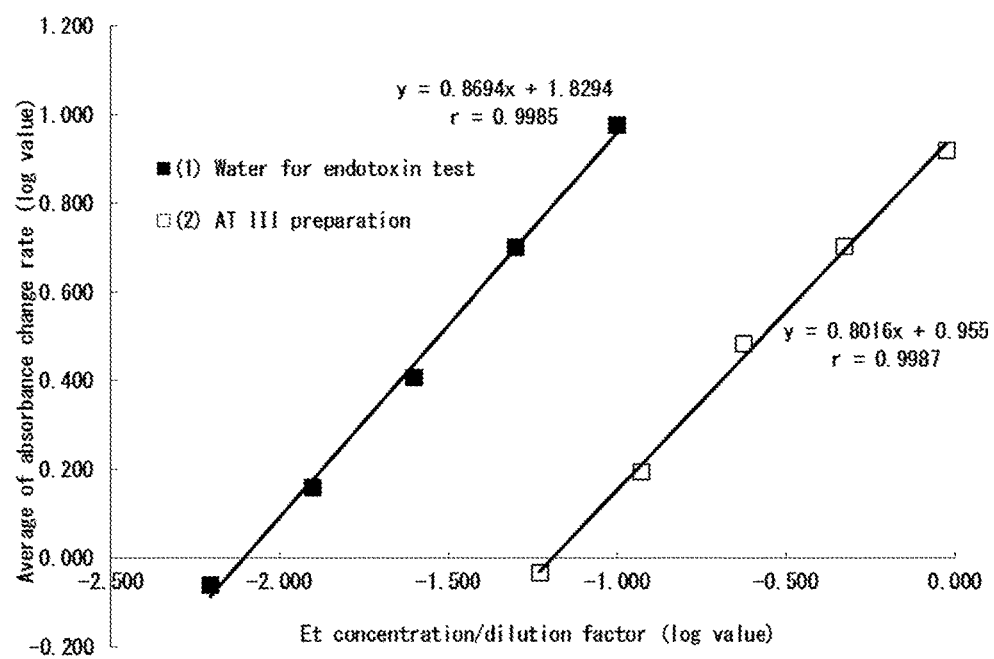

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Ile Glu Gly Arg
1

PRE-TREATMENT AGENT AND PRE-TREATMENT METHOD FOR ANTITHROMBIN III TO BE SUBJECTED TO LIMULUS TEST

CROSS REFERENCE TO RELATED APPLICATIONS

This application is a National Stage of International Application No. PCT/JP2013/085234 filed Dec. 27, 2013, claiming priority based on Japanese Patent Application No. 2012-287475, filed Dec. 28, 2012, the contents of all of which are incorporated herein by reference in their entirety.

TECHNICAL FIELD

The present invention relates to a pre-treatment agent for antithrombin III which is to be subjected to a detection test for a target substance (e.g., endotoxin) employing a *limulus* reagent; to a *limulus* reagent kit including the pre-treatment agent; to a method for preliminarily treating antithrombin III and a method for measuring a target substance (e.g., endotoxin) by use of a *limulus* reagent, using these pre-treatment agent and *limulus* reagent kit.

In the present invention, the following abbreviations may be employed.
Et: endotoxin
BG: (1→43)-β-D-glucan
AT III: antithrombin III

BACKGROUND ART

Endotoxin is a lipopolysaccharide which is present in the cell wall outer membrane of Gram-negative bacteria and is known as a strong pyrogen. Endotoxin is also known to cause various pathological conditions including not only fever but also shock and the like. Therefore, detection and quantitation of endotoxin is essential in pharmaceutical products such as an injection pharmaceutical preparation, water, medical devices, and the like, from the viewpoint of ensuring safety of pharmaceutical products and the like.

As has been known, a horseshoe crab undergoes blood clotting when it is infected with a Gram-negative bacterium. This phenomenon has been conventionally employed for the detection of endotoxin. That is, endotoxin can be determined by use of blood corpuscle extracts of horseshoe crab (i.e., *limulus* amebocyte lysate, hereinafter referred to as "LAL"). This method is called "*limulus* test," which employs a cascade reaction of a variety of proteins (all serine proteases) present in LAL, which reaction occurs via contact between endotoxin with LAL.

AT III is an anti-coagulant in blood and is used for the treatment of disseminated intravascular coagulation (DIC) or the like. Since AT III is a serine protease inhibitor, it inhibits the activities of proteins which are present in LAL and which are involved in the cascade reaction (Non-Patent Document 1). Thus, in some cases, a certain type of a specimen inhibits a *limulus* reagent. Such an inhibitory action may be avoided by diluting a specimen (Non-Patent Document 2). However, AT III exhibits a very strong inhibitory action on a *limulus* reagent, and therefore, in order to carry out *limulus* test of an AT III pharmaceutical preparation (injection), the preparation must be diluted at a dilution factor of 64 or higher (Non-Patent Document 2). Therefore, in consideration of the detection sensitivity of a *limulus* reagent (i.e. the lowest endotoxin concentration on the calibration curve), subjecting an AT III pharmaceutical preparation to *limulus* test has been considered to be difficult (Non-Patent Document 2). Actually, even at present, detection of endotoxin in specimens each containing AT III is performed through the rabbit pyrogen test (Non-Patent Document 1).

Non-Patent Document 1 discloses a method for determining Et in an AT III pharmaceutical preparation, in which method the AT III pharmaceutical preparation is 100-fold diluted; the diluted product is heated at 70° C. for 20 minutes as a pre-treatment; the pre-treated product is reacted with LAL; and Et is detected through the light scattering method. A technical feature of the method resides in employment of the light scattering method by means of a light scattering measurement apparatus instead of turbidimetric assay by means of a spectrophotometer, in order to realize a high sensitivity in Et detection. However, similar to the aforementioned case, the method requires dilution of a specimen at high dilution factor, and involves at least the following problems.

(1) Spectrophotometers are widely employed as a measurement apparatus for *limulus* test, and a light scattering measurement apparatus must be additionally provided and used for carrying out the light scattering method.

(2) The Japanese Pharmacopoeia specifies only turbidimetric assay and chromogenic assay as photometric assay methods of Et, and is silent to a light scattering method.

Patent Document 1 discloses an Et and BG assay method for biological samples, the method comprising bringing a biological sample into contact with an alkaline earth metal sulfate or an alkaline earth metal halide, heating the mixture as a pre-treatment, and then subjecting the pre-treated product to an assay by use of a *limulus* reagent.

Patent Document 2 discloses an Et and BG assay method for blood samples, the method comprising mixing a biological sample with a hexadimethrine compound, an alkali metal hydroxide, a nonionic surfactant, and an alkaline earth metal halide, heating the mixture as a pre-treatment, and then subjecting the pre-treated product to an assay by use of a *limulus* reagent.

Patent Document 3 discloses an Et assay method for a sample possibly containing AT III, the method comprising bringing a biological sample into contact with a carrier on which lipopolysaccharide-binding peptide and/or lipid A-binding peptide is immobilized to thereby recover Et via absorption into the carrier, and then subjecting the recovered Et to an assay by use of a *limulus* reagent or the like.

However, none of the aforementioned documents discloses or suggests subjecting AT III to a protein inactivation treatment as a pre-treatment in the co-presence of a divalent metal salt for carrying out *limulus* test of AT III.

PRIOR ART DOCUMENTS

Patent Documents

Patent Document 1: WO 2006/080448
Patent Document 2: Japanese Patent Application (kokai) No. Hei 6-70796
Patent Document 3: Japanese Patent Application (kokai) No. 2010-243342

Non-Patent Documents

Non-Patent Document 1: Endotoxin and Natural Immunity Research 15—Rapidly Developing Natural Immunity Research—, Igakutosho-shuppan Ltd., p. 27 to 30, 2012

Non-Patent Document 2: Endotoxin Research 12—New Development in Natural Immunity Research—, Igaku-tosho-shuppan Ltd., p. 93 to 97, 2009

SUMMARY OF THE INVENTION

Problems to be Solved by the Invention

An object of the present invention is to provide means for reducing reaction interference observed when AT III is subjected to *limulus* test, whereby *limulus* test of AT III can be carried out at high accuracy. The term "reaction interference" referred to herein refers to any action which is caused by a factor other than target substances of *limulus* test (e.g., Et and BG) and which affects the results of *limulus* test. Thus, "reaction interference" encompasses, for example, all actions affecting the results of *limulus* test caused by AT III itself, a component such as an additive or an impurity which is co-present with AT III, a component such as a reagent other than a pre-treatment agent which is co-present in the pre-treatment, and/or a component contained in a *limulus* reagent; such as an action of insolubilization of any of these components itself, an action of promoting or inhibiting the reaction of a *limulus* reagent, and an action of changing the micelle structure of Et or the steric structure of BG to thereby modify the activity of Et or BG (reactivity to Factor C or Factor G contained in a *limulus* reagent).

Means for Solving the Problems

The present inventors have conducted extensive studies so as to attain the aforementioned object, and have found that reaction interference observed when AT III is subjected to *limulus* test can be reduced by subjecting AT III to a protein inactivation treatment such as a thermal treatment or an acid treatment in the co-presence of a divalent metal salt, whereby *limulus* test of AT III can be carried out at high accuracy. The present invention has been accomplished on the basis of this finding.

Accordingly, the present invention encompasses the following modes.

[1]
A pre-treatment agent for antithrombin III to be subjected to *limulus* test,
which agent contains a divalent metal salt, and
which agent is used for subjecting antithrombin III to a protein inactivation treatment in the co-presence of the pre-treatment agent, before antithrombin III is subjected to *limulus* test.

[2]
The above-described pre-treatment agent, wherein the divalent metal salt is one or more metal salts selected from the group consisting of a divalent metal chloride, a divalent metal acetate, and a divalent metal sulfate.

[3]
The above-described pre-treatment agent, wherein the divalent metal constituting the divalent metal salt is one or more metals selected from the group consisting of magnesium, calcium, manganese, and zinc.

[4]
The above-described pre-treatment agent, wherein the concentration of the divalent metal ion derived from the divalent metal salt is 0.5 mM or higher when antithrombin III is co-present with the pre-treatment agent.

[5]
The above-described pre-treatment agent, wherein a target substance of the *limulus* test is endotoxin.

[6]
A *limulus* reagent kit for antithrombin III, the kit comprising the pre-treatment agent.

[7]
A pre-treatment method for antithrombin III to be subjected to *limulus* test, the method comprising subjecting antithrombin III to a protein inactivation treatment in the co-presence of the pre-treatment agent.

[8]
The above-described pre-treatment method, wherein the protein inactivation treatment is a thermal treatment or an acid treatment.

[9]
The above-described pre-treatment method, wherein the thermal treatment is performed at a temperature higher than 50° C.

[10]
The above-described pre-treatment method, wherein the acid employed in the acid treatment is hydrochloric acid.

[11]
A method for measuring a target substance of *limulus* test contained in antithrombin III, the method comprising preliminarily treating antithrombin III through the above-described pre-treatment method, and subjecting the preliminarily treated antithrombin III to *limulus* test.

[12]
A method for producing antithrombin III, the method comprising measuring the target substance of *limulus* test in antithrombin III through the above-described method.

BRIEF DESCRIPTION OF THE DRAWINGS

FIG. 1 A graph showing test results of parallel line assay.
FIG. 2 A graph showing test results of parallel line assay.
FIG. 3 A graph showing test results of parallel line assay.

MODES FOR CARRYING OUT THE INVENTION (1) The Pre-Treatment Agent of the Present Invention The pre-treatment agent of the present invention is a pre-treatment agent for AT III to be subjected to *limulus* test, which agent contains a divalent metal salt. The pre-treatment agent of the present invention is used for subjecting antithrombin III to a protein inactivation treatment in the co-presence of the pre-treatment agent of the present invention, before antithrombin III is subjected to *limulus* test.

The term "*limulus* test" referred to herein refers to a test for detecting (measuring) a target substance by use of a *limulus* reagent. The target substance may also be referred to as "target substance of *limulus* test (*limulus* test target substance)." The *limulus* test target substance is not particularly limited so long as it is a substance detectable by *limulus* test. The target substance is preferably Et or BG, and more preferably Et.

The "AT III" referred to herein is not particularly limited so long as it is a specimen containing AT III. The "AT III" referred to herein may consist of AT III, or may further contain a component other than AT III. The form of AT III is also not particularly limited. For example, AT III may be in the form of liquid, or may be in the form of solid such as a lyophilized product, powder, granules, or tablets.

An example of AT III is an injection pharmaceutical preparation of AT III. Specific examples of such injection pharmaceutical preparations include Neuart (registered trademark; product of Benesis Co., Ltd.), Anthrobin (product of The Chemo-Sero-Therapeutic Research Institute), and Nonthron (registered trademark; product of Nihon Pharmaceutical Co., Ltd.). When such an AT III injection pharmaceutical preparation is subjected to the pre-treatment method of the present invention and *limulus* test, undiluted solution thereof may be used as a specimen, a concentrated solution thereof may be used as a specimen, or a solution diluted at any dilution factor with an aqueous medium (e.g., water or buffer) may be used as a specimen. The term "undiluted solution" referred to herein refers to a solution containing AT III at a concentration of 50 Unit/mL, which is a common concentration when AT III is used as an injection pharmaceutical preparation. The "undiluted solution" may be obtained by dissolving AT III in an aqueous medium, according to the method described in a package insert of corresponding AT III injection pharmaceutical preparation. The term "concentrated solution" referred to herein refers to a solution containing AT III at a concentration higher than 50 Unit/mL. An example of the "concentrated solution" is an intermediate purified product obtained in a step of production of an AT III injection pharmaceutical preparation.

The dilution factor when undiluted solution is diluted with an aqueous medium is not particularly limited so long as a *limulus* test target substance can be detected. For example, the dilution factor is preferably higher than 1 and lower than 64, more preferably higher than 1 and 16 or lower, still more preferably higher than 1 and 10 or lower, yet more preferably higher than 1 and 4 or lower, particularly preferably higher than 1 and 2.5 or lower, remarkably preferably 1.1 to 2.5, particularly remarkably preferably 1.2 to 2.5. Notably, the term "dilution factor" referred to herein refers to the dilution fold of a reaction mixture in which a protein inactivation treatment is performed in the co-presence of the pre-treatment agent of the present invention, with respect to the aforementioned "undiluted solution." Thus, a dilution factor of "1" refers to the state that the AT III concentration of a reaction mixture in which a protein inactivation treatment is performed in the co-presence of the pre-treatment agent of the present invention is the same as the AT III concentration of the aforementioned "undiluted solution." In other words, a dilution factor of "1" refers to the state that the reaction mixture is the same as the undiluted solution, and also the state that the reaction mixture is not diluted and thereby contains AT III at a concentration of 50 Unit/mL.

AT III may also be a recombinant protein. The recombinant AT III may be obtained through gene expression in a host cell. Expression in a host cell may be performed through a conventional method. For example, expression in a host cell may be performed through a method by Yamada et al. (WO 2005/035563). The amino acid sequence of AT III and the nucleotide sequence of a gene encoding AT III may be obtained from a known database. Examples of such a known database include NCBI (http://www.ncbi.nlm.nih.gov/). The recombinant protein to be expressed may be a protein having an amino acid sequence identical to that of a native AT III. In addition, the recombinant protein to be expressed may be a variant of a native AT III, so long as functions of AT III are maintained. Such a variant encompasses homologues and artificially modified products of known AT III.

The "divalent metal salt" referred to herein is not particularly limited so long as it is a metal salt recognized as a divalent metal salt in the art of the present invention. Examples of the divalent metal salt include a divalent metal fluoride, a divalent metal chloride, a divalent metal bromide, a divalent metal iodide, a divalent metal hydroxide, a divalent metal cyanide, a divalent metal nitrate, a divalent metal nitrite, a divalent metal hypochlorite, a divalent metal chlorite, a divalent metal chlorate, a divalent metal perchlorate, a divalent metal permanganate, a divalent metal acetate, a divalent metal hydrogencarbonate, a divalent metal dihydrogen phosphate, a divalent metal hydrogensulfate, a divalent metal hydrogensulfide salt, a divalent metal thiocyanate, a divalent metal oxide, a divalent metal sulfide, a divalent metal peroxide, a divalent metal sulfate, a divalent metal sulfite, a divalent metal thiosulfate, a divalent metal carbonate, a divalent metal chromate, a divalent metal bichromate, a divalent metal monohydrogen phosphate, and a divalent metal phosphate. As the divalent metal salt, a single kind of metal salt may be used solely, or two or more kinds of metal salts may be used in combination. The divalent metal salt is preferably, for example, one or more metal salts selected from the group consisting of a divalent metal chloride, a divalent metal acetate, and a divalent metal sulfate.

The divalent metal salt may be a metal salt which provides a divalent metal ion when AT III is co-present with the pre-treatment agent of the present invention. The state "when AT III is co-present with the pre-treatment agent of the present invention" specifically refers to the duration in which the protein inactivation treatment mentioned below is performed. The divalent metal salt may be, for example, a metal salt which provides a divalent metal ion through dissolution in an aqueous medium. Examples of the aqueous medium include water and a buffer.

The "divalent metal" referred to herein is not particularly limited so long as it is a metal recognized as a divalent metal in the art of the present invention. The "divalent metal" may refer to a metal which provides a divalent metal ion when ionized. Examples of the divalent metal include beryllium, magnesium, calcium, strontium, barium, radium, cadmium, nickel, zinc, copper, mercury, iron, cobalt, tin, lead, and manganese. As the divalent metal, a single kind of metal may be used solely, or two or more kinds of metals may be used in combination. The divalent metal is preferably, for example, one or more metals selected from the group consisting of magnesium, calcium, manganese, and zinc.

Specific examples of the divalent metal salt include magnesium sulfate ($MgSO_4$), magnesium chloride ($MgCl_2$), magnesium acetate ($Mg(CH_3COO)_2$), calcium chloride ($CaCl_2$), calcium acetate ($Ca(CH_3COO)_2$), manganese sulfate ($MnSO_4$), and zinc sulfate ($ZnSO_4$). The pre-treatment agent of the present invention may contain, for example, only magnesium sulfate ($MgSO_4$) as a divalent metal salt. Alternatively, the pre-treatment agent of the present invention may contain, for example, magnesium sulfate ($MgSO_4$) and one or more other divalent metal salts.

Also, the pre-treatment agent of the present invention may further contain an additional component. The "additional component" is not particularly limited so long as it is acceptable for use in a reagent or diagnostic agent. For example, components which are incorporated into a reagent or a diagnostic agent may be employed as the "additional component". Examples of the "additional component" include an alkali metal chloride, an alkali metal acetate, an alkali metal sulfate, a surfactant, and an additive. Examples of the additive include, but are not limited to, a stabilizer, an emulsifying agent, an osmo-regulating agent, a buffer, a tonic agent, a preservative, a pH-adjusting agent, a colorant, an excipient, a condensing agent, a lubricant, and a disintegrant.

The form of the pre-treatment agent of the present invention is not particularly limited. For example, the pre-treatment agent of the present invention may be provided as liquid preparation, or may be provided as solid preparation for dissolution upon use; such as powder, granules, or tablets, may be employed. Also, the pre-treatment agent of the present invention may be provided as a microplate retaining the pre-treatment agent of the present invention in the wells thereof. Such a microplate may be obtained through, for example, dispensing the pre-treatment agent of the present invention which has been prepared in the form of liquid into the wells and drying the plate. In the case where the pre-treatment agent of the present invention is provided as a liquid preparation, the pre-treatment agent of the present invention may be provided as a frozen product, or may be provided as a liquid product (melting state).

In the pre-treatment agent of the present invention, the divalent metal salt may be present as a salt form, an ionic form, or a mixture thereof. The state that "the pre-treatment agent of the present invention contains a divalent metal salt" encompasses all three cases.

Except for incorporation of a divalent metal salt, the pre-treatment agent of the present invention may be produced through the same technique as generally employed in production of reagents and diagnostic agents.

The concentration of the divalent metal salt concentration in the pre-treatment agent of the present invention is not particularly limited, and the concentration may be appropriately tuned in accordance with various conditions such as the type of the divalent metal salt and the amount used of the pre-treatment agent of the present invention. The concentration of the divalent metal salt in the pre-treatment agent of the present invention may be, for example, 0.001 mass % or higher, 0.01 mass % or higher, 0.1 mass % or higher, 1 mass % or higher, 5 mass % or higher, 10 mass % or higher, 30 mass % or higher, or 50 mass % or higher. The concentration of the divalent metal salt in the pre-treatment agent of the present invention may be, for example, 100 mass % or lower, 50 mass % or lower, 30 mass % or lower, 10 mass % or lower, 5 mass % or lower, or 1 mass % or lower.

The amount used of the pre-treatment agent of the present invention is not particularly limited, and the amount may be appropriately tuned in accordance with various conditions such as the type and the concentration of the divalent metal salt. The pre-treatment agent of the present invention may be used so that, for example, the concentration of the divalent metal ion derived from the divalent metal salt (hereinafter the concentration may be referred to as "divalent metal ion concentration during treatment") falls within the below-exemplified ranges when AT III is co-present with the pre-treatment agent of the present invention. The "concentration when AT III is co-present with the pre-treatment agent of the present invention" specifically refers to the concentration of the divalent metal ion in the reaction system where the protein inactivation treatment mentioned below is performed. The divalent metal ion concentration during treatment is not particularly limited so long as the effect of the pre-treatment of the present invention can be attained, and the concentration is preferably, for example, 0.5 mM or higher. The divalent metal ion concentration during treatment is, for example, preferably 0.5 mM to 100 mM, more preferably 0.5 mM to 50 mM, still more preferably 0.5 mM to 25 mM, yet more preferably 5 mM to 25 mM, particularly preferably 5 mM to 12.5 mM. Notably, in the case where the pre-treatment agent of the present invention contains two or more divalent metal salts, the "divalent metal ion concentration during treatment" means the total concentration of the divalent metal ion(s) derived from these divalent metal salts.

Through a pre-treatment of AT III by use of the pre-treatment agent of the present invention, reaction interference observed when AT III is subjected to *limulus* test can be reduced, and thus, *limulus* test of AT III can be carried out at high accuracy.

(2) The Kit of the Present Invention

The kit of the present invention is a *limulus* reagent kit which comprises the pre-treatment agent of the present invention, as a component. The kit of the present invention may further comprise an additional component. Examples of the "additional component" include, but are not limited to, a *limulus* reagent, a substrate for detection of *limulus* reaction, buffer, distilled water, a standard substance (e.g., Et or BG), and a microplate.

The *limulus* reagent used in the present invention is not particularly limited so long as the reagent contains a protein or proteins involved in a cascade reaction corresponding to a *limulus* test target substance. An example of the *limulus* reagent is blood corpuscle extracts of horseshoe crab (LAL; lysate reagent). LAL may be obtained from blood of a horseshoe crab as a raw material through a conventional method. LAL may be used after appropriate fractionation and/or purification. Any types of horseshoe crabs may be employed as the origin of LAL. Example of the horseshoe crab include *Tachypleus tridentatus* (Japanese horseshoe crab), *Limulus polyphemus* (American horseshoe crab), *Carcinoscorpius rotundicauda* (Southeast Asian horseshoe crab), and *Tachypleus gigas* (Southeast Asian horseshoe crab).

Examples of the *limulus* reagent employing a lysate derived from *Limulus polyphemus* include Endospecy (registered trademark) ES-50M (product of Seikagaku Corporation), Pyrochrome (product of Associates of Cape Cod, Inc.), Pyrotell (registered trademark)-T (product of Associates of Cape Cod, Inc.), Pyrotell (registered trademark) multi-test (product of Associates of Cape Cod, Inc.), Kinetic-QCL (product of Lonza Walkerrsville, Inc.) and Endochrome-K (product of Charles River Laboratories, Inc.).

Examples of the *limulus* reagent also include artificially reconstituted *limulus* reagents. The reconstituted *limulus* reagent is not particularly limited so long as the reagent contains a protein or proteins involved in a cascade reaction corresponding to a *limulus* test target substance. Proteins involved in the cascade reaction are also collectively referred to as "factors." The term "cascade reaction" referred to herein refers to a series of reactions which proceed due to the presence of a *limulus* test target substance. For example, when a substance which activates Factor C (e.g., Et) is present, a series of the following reactions proceed: Factor C is activated by the substance to thereby form activated Factor C; the activated factor C activates Factor B to thereby form activated Factor B; and the activated Factor B activates Pro-clotting enzyme to thereby form the corresponding Clotting enzyme. That is, in the case where a substance which activates Factor C (e.g., Et) is a target substance, it is sufficient that the reconstituted *limulus* reagent contains Factor C, Factor B, and Pro-clotting enzyme, as factors constituting the cascade reaction. When a substance which activates Factor G (e.g., BG) is present, a series of the following reactions proceed: Factor G is activated by the substance to thereby form activated Factor G; and the activated Factor G activates Pro-clotting enzyme to thereby form the corresponding Clotting enzyme. That is, in the case where a substance which activates Factor G (e.g., BG) is a target substance, it is sufficient that the reconstituted *limulus* reagent contains Factor G and Pro-clotting enzyme, as factors constituting the cascade reaction. The progress of a cascade reaction can be determined by detecting Clotting enzyme by use of the below-mentioned detection substrate for *limulus* reaction.

In the case where a detection substrate that is able to detect an intermediate stage of a cascade reaction is employed as the below-mentioned detection substrate for *limulus* reaction, it is sufficient that the reconstituted *limulus* reagent contains a factor or factors involved in from the start of the cascade reaction to the relevant intermediate stage. Specifically, for example, in the case where a substance which activates Factor C (e.g., Et) is a target substance, and a detection substrate for *limulus* reaction that is able to detect activated Factor C is used, it is sufficient that the reconstituted *limulus* reagent contains Factor C.

Each of factors contained in a reconstituted *limulus* reagent may be a native protein or a recombinant protein.

Native factors may each be obtained from amebocyte lysates (LAL) of the aforementioned various horseshoe crabs. These factors may each be purified to a desired degree before use. Purification may be performed through, for example, a known technique (Nakamura T. et al., J. Biochem. 1986 March; 99(3): 847-57).

The factors may each also be obtained through expression in a host cell. Expression in a host cell may be performed through a conventional method. For example, expression in a host cell may be performed through a method by Mizumura et al., (WO 2012/118226). The amino acid sequence of each factor and the nucleotide sequence of a gene encoding the factor may be obtained from a known database. Examples of such a known database include NCBI (http://www.ncbi.nlm.nih.gov/). The thus-expressed recombinant proteins may each be purified to a desired degree before use, as necessary.

By appropriately combining the factors, a reconstituted *limulus* reagent can be obtained. The factors contained in the reconstituted *limulus* reagent may be all native factors, all recombinant proteins, or any combination thereof. Also, the reconstituted *limulus* reagent may be an appropriate combination of the factor or factors with a whole LAL, or with LAL which has been subjected to appropriate fractionation and/or purification or the like.

The detection substrate for *limulus* reaction (hereinafter may also be referred to simply as "detection substrate") refers to a substrate for detecting the progress of the cascade reaction.

Examples of the detection substrate include coagulogen. Coagulogen is a detection substrate with respect to Clotting enzyme, which is the final product of the cascade reaction. When coagulogen come into contact with Clotting enzyme, a coagulated product, coagulin, is formed. The progress of the coagulation reaction can be determined by measuring the turbidity of the reaction mixture or by observing gel formation. Coagulogen can be recovered from blood corpuscle extracts of horseshoe crab (LAL). Since the nucleotide sequence of the gene encoding coagulogen has been determined (Miyata et al, Protein Nucleic acid Enzyme, extra issue, No. 29; p. 30-43; 1986), coagulogen can also be produced genetically according to a conventional technique.

The detection substrate may be a synthetic substrate. The synthetic substrate is not particularly limited so long as it has a property suitable for detection of the progress of the cascade reaction. The "property suitable for detection of the progress of the cascade reaction" may be, for example, a property for detecting the presence of Clotting enzyme or a property for detecting an intermediate stage of the cascade reaction. Examples of the "property for detecting the presence of Clotting enzyme" include a property of coloring by an enzymatic reaction of Clotting enzyme and a property of generating fluorescence by an enzymatic reaction of Clotting enzyme. Examples of the "property for detecting an intermediate stage of the cascade reaction" include a property of coloring by an enzymatic reaction of activated Factor C or the like, and a property of generating fluorescence by an enzymatic reaction of activated Factor C or the like. Examples of the synthetic substrate include a substrate represented by formula X—Y—Z (wherein X represents a protection group, Y represents a peptide, and Z represents a dye linked to Y via amide bond). When a substance which activates Factor C (e.g., Et) is present in the reaction system containing Factor C, Factor B, and Pro-clotting enzyme, an amide linkage Y—Z is cleaved by the enzymatic reaction of Clotting enzyme, which is yielded by the cascade reaction, to release the dye Z, whereby coloring occurs or fluorescence is generated. In the case where the reaction system containing Factor G and Pro-clotting enzyme is employed, or in the case where an intermediate stage of the cascade reaction is detected, it is sufficient that the dye Z is released by Clotting enzyme or by a protein formed yielded at the intermediate stage of the cascade reaction, respectively. The protective group X is not particularly limited, and a known protective group for peptide may be suitably used. Examples of such a protective group include a t-butoxycarbonyl group and a benzoyl group. The dye Z is not particularly limited, and it may be a dye detectable under visible light or may be a fluorescent dye. Examples of the dye Z include p-nitroaniline (pNA), 7-methoxycoumarin-4-acetic acid (MCA), 2,4-dinitroaniline (DNP), and Dansyl dyes. Examples of the peptide Y include Leu-Gly-Arg (LGR), Ile-Glu-Gly-Arg (IEGR) (SEQ ID NO: 1), Val-Pro-Arg (VPR), and Asp-Pro-Arg (DPR). These synthetic substrates may each be used for detecting the presence of Clotting enzyme, or for detecting an intermediate stage of the cascade reaction. Among these synthetic substrates, suitable one may be appropriately selected and used depending on the detection target. For example, from the viewpoint of substrate specificity, a substrate comprising LGR as peptide Y can be suitably used for detecting Clotting enzyme, and a substrate comprising VPR or DPR as peptide Y can be suitably used for detecting activated Factor C. The released dye Z may be determined through a technique in accordance with the property of the dye.

When blood corpuscle extracts of horseshoe crab (LAL) is used as a *limulus* reagent, coagulogen, which is intrinsically contained in LAL, may be used as a detection substrate. Also, an appropriately selected detection substrate may be used in combination with LAL.

When a reconstituted *limulus* reagent is used as a *limulus* reagent, an appropriately selected detection substrate may be combined with the reconstituted *limulus* reagent.

In the kit of the present invention, these factors and detection substrates may be present as a mixture thereof, as separate components, or as separate arbitrary combinations thereof.

Through the pre-treatment of AT III with the kit of the present invention, reaction interference observed when AT III is subjected to *limulus* test can be reduced, whereby *limulus* test of AT III can be carried out at high accuracy.

(3) The Pre-Treatment Method of the Present Invention

The pre-treatment method of the present invention is a method for preliminarily treating AT III to be subjected to *limulus* test, which method comprises subjecting AT III to a protein inactivation treatment in the co-presence of the pre-treatment agent of the present invention.

The "protein inactivation treatment" referred to herein is not particularly limited so long as it is a treatment of inactivating AT III, or more specifically a treatment of inactivating AT III to such an extent that *limulus* test is not inhibited. Examples of the protein inactivation treatment include, but are not limited to, a thermal treatment, an acid treatment, and an alkali treatment. As the protein inactivation treatment, a single kind of treatment may be used solely, or two or more kinds of treatments may be used in combination.

The protein inactivation treatment may be performed in, for example, an aqueous medium such as water or a buffer. That is, the protein inactivation treatment may be performed in, for example, an aqueous medium containing AT III in the co-presence of the pre-treatment agent of the present invention.

The term "thermal treatment" referred to herein refers to heating of AT III in the co-presence of the pre-treatment agent of the present invention. The method for heating is not particularly limited, and a method using a heating apparatus such as a heat block, a water bath, an air bath, or a microwave oven is preferably employed. The temperature of the thermal treatment is not particularly limited so long as protein inactivation occurs. For example, the temperature of the thermal treatment is generally higher than 50° C. The temperature of the thermal treatment is preferably, for example, 55° C. to 100° C., more preferably 55° C. to 95° C., still more preferably 60° C. to 90° C., yet more preferably 65° C. to 85° C., particularly preferably 65° C. to 75° C. The time of the thermal treatment is not particularly limited so long as protein inactivation occurs. For example, the time of the thermal treatment is preferably 1 minute or longer. The time of the thermal treatment is, for example, preferably 1 minute to 2 hours, more preferably 1 minute to 1 hour, still more preferably 5 minutes to 30 minutes, yet more preferably 5 minutes to 20 minutes, particularly preferably 5 minutes to 15 minutes.

The term "acid treatment" referred to herein refers to a treatment of bringing AT III co-present with the pre-treatment agent of the present invention into contact with an acid. Examples of the acid used in the acid treatment include, but are not limited to, hydrochloric acid, sulfuric acid, and nitric acid. Of these, hydrochloric acid is preferred. The amount of acid added may be appropriately tuned in accordance with various conditions such as the type of acid. The amount of acid added may be, for example, such an amount that the acid concentration of the reaction system at the acid treatment becomes 0.001 N to 1 N, preferably 0.01 N to 0.5 N, more preferably 0.01 N to 0.1 N. The time of acid treatment is not particularly limited so long as protein inactivation occurs, and it may be a time generally employed in an acid treatment. The time of acid treatment may be, for example, 0.1 seconds to 2 hours.

The term "alkali treatment" referred to herein refers to a treatment of bringing AT III co-present with the pre-treatment agent of the present invention into contact with an alkali. Examples of the alkali used in the alkali treatment include, but are not limited to, sodium hydroxide and potassium hydroxide. Of these, sodium hydroxide is preferred. The amount of alkali added may be appropriately tuned in accordance with various conditions such as the type of alkali. The amount of alkali added may be, for example, such an amount that the alkali concentration of the reaction system at the alkali treatment becomes 0.001 N to 1 N, preferably 0.01 N to 0.5 N, more preferably 0.01 N to 0.1 N. The time of alkali treatment is not particularly limited so long as protein inactivation occurs, and it may be a time generally employed in an alkali treatment. The time of alkali treatment may be, for example, 0.1 seconds to 2 hours.

The pre-treatment method of the present invention may further include a step other than the protein inactivation treatment.

For example, an additional treatment may be appropriately performed on AT III before the protein inactivation treatment. For example, a processing treatment of AT III, such as particle size reduction of AT III dry powder, may be performed. Also, AT III may be diluted or concentrated. These additional treatments may each be performed before AT III is made to be co-present with the pre-treatment agent of the present invention, or after AT III is made to be co-present with the pre-treatment agent of the present invention and before the protein inactivation treatment.

Also, after the protein inactivation treatment, a post treatment may be appropriately performed. The post treatment may be, for example, a treatment of preventing inhibition of *limulus* test when preliminarily treated AT III is subjected to *limulus* test. For example, when a thermal treatment has been performed as a protein inactivation treatment, the thus-treated product may be cooled. Also, for example, when an acid treatment is performed as a protein inactivation treatment, the thus-treated product may be neutralized with alkali. Also, for example, when an alkali treatment is performed as a protein inactivation treatment, the thus-treated product may be neutralized with acid. Also, for example, such a treated product may be diluted or concentrated.

Through the pre-treatment of AT III by the pre-treatment method of the present invention, reaction interference observed when AT III is subjected to *limulus* test can be reduced, whereby *limulus* test of AT III can be carried out at high accuracy.

(4) Assay Method of the Present Invention

The assay method of the present invention is a method for measuring a *limulus* test target substance contained in AT III, the method comprising preliminarily treating AT III through the pre-treatment method of the present invention, and subjecting the preliminarily treated AT III to *limulus* test.

*Limulus* test may be carried out through, for example, a known technique. Examples of such a known technique include chromogenic assay, turbidimetric assay, and gel-clot assay.

Specifically, *limulus* test can be carried out by bringing AT III into contact with a *limulus* reagent. When a *limulus* test target substance is present in AT III, a cascade reaction proceeds. Thus, the *limulus* test target substance in AT III can be measured by determining the progress of the cascade reaction. In *limulus* test, the factors may be contained in the reaction system at the start of the step of bringing AT III into contact with the *limulus* reagent, or may be successively added to the reaction system.

The progress of the cascade reaction can be determined by use of a detection substrate. That is, the progress of the cascade reaction can be determined by measuring the response (coloring, coagulation, etc.) of the detection substrate depending on the type of the detection substrate. The detection substrate may be added to the reaction system in any timing. For example, the detection substrate may be contained in the reaction system at the start of the step of bringing AT III into contact with a *limulus* reagent, or may be added during or after the step. In the case where a *limulus* reagent containing a detection substrate is used, no additional detection substrate needs to be added to the reaction system.

The assay method of the present invention may further comprise any additional step, so long as a cascade reaction proceeds when AT III contains a *limulus* test target substance. For example, as described above, the assay method of the present invention may further comprise a step of adding a detection substrate to the reaction system. Also, the assay method of the present invention may further comprise a step of transforming data obtained through measurement into different data. An example of the step of transforming data obtained through measurement into different data is a step of calculating the amount of a *limulus* test target substance present in AT III on the basis of the data obtained through measurement.

In the assay method of the present invention, any reaction is preferably performed in an aqueous medium such as water or a buffer.

According to the assay method of the present invention, reaction interference observed when AT III is subjected to *limulus* test can be reduced, whereby *limulus* test of AT III can be carried out at high accuracy.

Thus, there can be obtained AT III which has been confirmed to be free from contamination of a *limulus* test target substance. That is, the present invention also provides a method for producing AT III, the method comprising measuring a *limulus* test target substance in AT III through the assay method of the present invention. The thus-produced AT III may be provided in any form, such as an injection pharmaceutical preparation.

EXAMPLES

The present invention will next be described more specifically by way of examples, which should not be construed as limiting the technical scope of the present invention. Notably, water, reagents, plastic articles, glass articles, and others used in all tests described in the Examples were ensured to contain no endotoxin and no reaction interference factor with respect to the reaction of a *limulus* reagent.
<Definition of Et Recovery>

In tests carried out through chromogenic assay or turbidimetric assay, the mean recovery of the added Et (Et recovery) was calculated through the following procedure. Specifically, as well as *limulus* test for an AT III specimen spiked with a known amount of Et, *limulus* test for a specimen employing an equivolume of water instead of AT III and spiked with Et in the same way was concurrently carried out as a positive control. The absorbance change rate (mAbs/min) of the AT III specimen was divided by the absorbance change rate of the positive control, and thus-obtained value was converted to a percentage, to thereby obtain the Et recovery. In the case that AT III or water is contaminated with Et, the Et recovery may be calculated after subtraction of a contamination-equivalent value from a corresponding measurement. That is, the concept "Et recovery" may refer to the ratio (%) of the amount of Et actually detected in an AT III specimen to the amount of Et to be theoretically detected in the case where reaction interference by AT III is absent.

Referential Example 1

Et Recovery Test for AT III, Investigated Through Dilution and Heating Method

An undiluted 50-Unit/mL AT III pharmaceutical preparation (Neuart (registered trademark); product of Benesis; hereinafter the same shall apply), and water-diluted preparations thereof at dilution factors of 4, 16, 64, and 256 were provided. To each of the undiluted and diluted preparations (0.4 mL), a standard solution (0.04 mL) of Et (JPRSE: Japanese Pharmacopoeia endotoxin standard sample; hereinafter the same shall apply), prepared to a concentration of 0.5 EU/mL, was added. The thus-prepared mixtures were each vigorously agitated for one minute by means of a test tube mixer. Subsequently, each solution (0.2 mL) was dispensed to another container, and heated at 70° C. for 10 minutes by means of a heat block. Thereafter, the thus-heated solution (0.05 mL) was dispensed to a microplate, and an Et assay reagent for chromogenic assay (Endospecy (registered trademark) ES-50M; product of Seikagaku Corporation); hereinafter the same shall apply) (0.05 mL) was added to the microplate. The microplate was vigorously agitated for one minute by means of a well-reader provided with functions of a thermostat bath and agitation (Well-reader MP-96; product of Seikagaku Corporation; hereinafter the same shall apply). Thereafter, the change over time in absorbance was monitored at a measurement wavelength of 405 nm and a reference wavelength of 492 nm, while the microplate was heated at 37° C. for 30 minutes, and then the Et recovery was calculated. Table 1 shows the results.

TABLE 1

Results of Et detection in AT III through dilution and heating method

| Dilution factor | Et recovery |
|---|---|
| ×1 | 7.3% |
| ×4 | 5.8% |
| ×16 | 9.4% |
| ×64 | 120.0% |
| ×256 | 100.3% |

As shown in Table 1, when the dilution factor was 16 or lower, the Et recovery was lower than 10%, failing to detect Et at high accuracy. In contrast, when the dilution factor was 64 or higher, the Et recovery of about 100% was attained. The results were virtually the same as previously reported results of the dilution heating method (Non-Patent Document 1).

Example 1

Et Recovery Test, Wherein Thermal Treatment was Performed in the Presence of Magnesium Sulfate or Calcium Chloride A 0.5-EU/mL Et standard solution (0.1 mL) was added to a 25-Unit/mL AT III pharmaceutical preparation (AT III pharmaceutical preparation twice diluted with water) (0.9 mL), and the mixture was vigorously agitated for one minute by means of a test tube mixer. Subsequently, the mixture (0.18 mL) was dispensed to another container, and 15.6 mM, 125 mM, 250 mM, 500 mM, or 1,000 mM aqueous $MgSO_4$ (0.02 mL), or 15.6 mM, 56 mM, 125 mM, 250 mM, or 500 mM aqueous $CaCl_2$ (0.02 mL) was added thereto, followed by vigorously agitating for one minute by means of a test tube mixer. Each solution was heated for 10 minutes at 70° C. by means of a heat block, and the solution was immediately cooled with ice. The solution was returned to room temperature, and an aliquot (0.05 mL) thereof was dispensed to a microplate. Endospecy ES-50 M (0.05 mL) was added to the microplate, and the microplate was vigorously agitated for one minute by means of a well-reader. Thereafter, the change over time in absorbance was monitored at a measurement wavelength of 405 nm and a reference wavelength of 492 nm, while the microplate was heated at 37° C. for 30 minutes, and then the Et recovery was calculated. Tables 2 and 3 show the results. In the tables, "MgSO$_4$ concentration" and "CaCl$_2$ concentration" are those of each reaction mixture during the thermal treatment. The dilution factor of the AT III pharmaceutical preparation employed in Example 1 was about 2.5.

TABLE 2

Results of Et detection in the case of thermal treatment in the co-presence of magnesium sulfate

| MgSO$_4$ concentration | Et recovery |
|---|---|
| 1.56 mM | 0.0% |
| 12.5 mM | 95.0% |
| 25 mM | 108.0% |
| 50 mM | 99.9% |
| 100 mM | 93.7% |

TABLE 3

Results of Et detection in the case of thermal treatment in the co-presence of calcium chloride

| CaCl$_2$ concentration | Et recovery |
|---|---|
| 1.56 mM | 6.4% |
| 5.6 mM | 75.0% |
| 12.5 mM | 52.4% |
| 25 mM | 48.0% |
| 50 mM | 13.1% |

As shown in Tables 2 and 3, in contrast to the case of the dilution and heating method, when AT III and Et were subjected to a thermal treatment in the co-presence of magnesium sulfate or calcium chloride, Et could be detected at high accuracy without being diluted at a dilution factor of 64 or higher. Particularly, when the magnesium sulfate concentration was 12.5 mM or higher, Et could be detected at high accuracy.

Example 2

Investigation into Type of Divalent Metal Salts

A 0.5-EU/mL Et standard solution (0.22 mL) was added to a 50-Unit/mL AT III pharmaceutical preparation (0.2 mL), and the mixture was vigorously agitated for one minute by means of a test tube mixer. Subsequently, water (1.8 mL) was added thereto, and the mixture was vigorously agitated for one minute by means of a test tube mixer. An aliquot (0.1 mL) of the mixture was dispensed another container. A 50 mM or 5 mM aqueous solution of a divalent metal salt was added in a 1/10 amount (0.011 mL) thereto, and the mixture was vigorously agitated for one minute by means of a test tube mixer. Each solution was heated for 10 minutes at 70° C. by means of a heat block, and the solution was immediately cooled with ice. The solution was returned to room temperature, and an aliquot (0.05 mL) thereof was dispensed to a microplate. Endospecy ES-50 M (0.05 mL) was added to the microplate, and the microplate was vigorously agitated for one minute by means of a well-reader. Thereafter, the change over time in absorbance was monitored at a measurement wavelength of 405 nm and a reference wavelength of 492 nm, while the microplate was heated at 37° C. for 30 minutes, and then the Et recovery was calculated. Table 4 shows the results. In the table, the divalent metal salt concentration is that of the reaction mixture during the thermal treatment. The dilution factor of the AT III pharmaceutical preparation employed in Example 2 was about 12.

TABLE 4

Results of Et detection in the case of thermal treatment in the co-presence of a divalent metal salt

| Co-present divalent metal salt | Et recovery |
|---|---|
| 0.5 mM Mg (CH$_3$COO)$_2$ | 56.8% |
| 5.0 mM Mg (CH$_3$COO)$_2$ | 104.7% |
| 0.5 mM MgCl$_2$ | 11.1% |
| 5.0 mM MgCl$_2$ | 106.2% |
| 0.5 mM Ca (CH$_3$COO)$_2$ | 75.7% |
| 5.0 mM Ca (CH$_3$COO)$_2$ | 84.6% |
| 0.5 mM MnSO$_4$ | 110.7% |
| 5.0 mM MnSO$_4$ | 88.1% |
| 0.5 mM ZnSO$_4$ | 105.7% |
| 5.0 mM ZnSO$_4$ | 15.7% |

As shown in Table 4, Et could be detected in the case where AT III was subjected to a thermal treatment in the co-presence of Mg(CH$_3$COO)$_2$, MgCl$_2$, Ca(CH$_3$COO)$_2$, MnSO$_4$, or ZnSO$_4$.

Example 3

Investigation into Temperature and Time of Thermal Treatment

A 0.5-EU/mL Et standard solution (0.1 mL) was added to a 50-Unit/mL AT III pharmaceutical preparation (0.9 mL), and the mixture was vigorously agitated for one minute by means of a test tube mixer. Subsequently, an aliquot (0.18 mL) of the mixture was dispensed another container. Subsequently, 200 mM aqueous CaCl$_2$ (0.02 mL) was added thereto, and the mixture was vigorously agitated for one minute by means of a test tube mixer. Each solution was placed on ice or heated at 37° C., 50° C., 60° C., 70° C., 80° C., or 90° C. for 5 minutes, 10 minutes, or 20 minutes by means of a heat block. In the case of heating, the solution was cooled with ice immediately after completion of heating. Each solution was returned to room temperature, and an aliquot (0.05 mL) thereof was dispensed to a microplate. Endospecy ES-50 M (0.05 mL) was added to the microplate, and the microplate was vigorously agitated for one minute by means of a well-reader. Thereafter, the change over time in absorbance was monitored at a measurement wavelength of 405 nm and a reference wavelength of 492 nm, while the microplate was heated at 37° C. for 30 minutes, and then the Et recovery was calculated. Table 5 shows the results. The CaCl$_2$ concentration of the reaction mixture during the thermal treatment was 20 mM. The dilution factor of the AT III pharmaceutical preparation employed in Example 3 was about 1.2.

TABLE 5

Results of Et detection in the case of thermal treatment under various conditions

| Temp. | Time | Et recovery |
|---|---|---|
| 0° C. | 10 min. | 0.0% |
| 37° C. | 5 min. | 0.0% |
|  | 10 min. | 0.0% |
| 50° C. | 10 min. | 0.0% |
| 60° C. | 5 min. | 35.7% |
|  | 10 min. | 46.3% |
| 70° C. | 5 min. | 52.3% |
|  | 10 min. | 61.9% |
|  | 20 min. | 68.6% |
| 80° C. | 10 min. | 57.9% |
| 90° C. | 10 min. | 56.5% |

As shown in Table 5, when the thermal treatment was performed at 60° C. or higher, Et could be detected. Also, when the thermal treatment was performed for 5 minutes or longer, Et could be detected. Based on the results obtained for heating at the tested temperature (60° C., 70° C., 80° C., or 90° C.) for 10 minutes, a thermal treatment temperature of 70° C., at which the highest Et recovery was obtained, was conceived to be preferred.

Referential Example 2

Investigation into effect of addition of divalent metal salt after thermal treatment A 0.5-EU/mL Et standard solution (0.1 mL) was added to water (0.9 mL) or to a 4-fold or 16-fold water-diluted 50-Unit/mL AT III pharmaceutical preparation (0.9 mL), and the mixture was vigorously agitated for one minute by means of a test tube mixer. Subsequently, an aliquot (0.18 mL) of the mixture was dispensed another container, and each mixture was placed on ice or heated at 70° C. for 10 minutes by means of a heat block. In the case of heating, the solution was cooled with ice immediately after completion of heating. Each solution was returned to room temperature. Thereafter, water or 7 mM, 28 mM, or 112 mM aqueous $CaCl_2$ (0.02 mL) was added thereto, and the mixture was vigorously agitated for one minute by means of a test tube mixer. An aliquot (0.05 mL) thereof was dispensed to a microplate. Endospecy ES-50 M (0.05 mL) was added to the microplate, and the microplate was vigorously agitated for one minute by means of a well-reader. Thereafter, the change over time in absorbance was monitored at a measurement wavelength of 405 nm and a reference wavelength of 492 nm, while the microplate was heated at 37° C. for 30 minutes, and then the Et recovery was calculated. Table 6 shows the results.

TABLE 6

Results of Et detection in the case of adding divalent metal salt after thermal treatment

| Dilution factor | $CaCl_2$ concentration | Et recovery |
| --- | --- | --- |
| ×4 | 0 mM | 8.0% |
|  | 0.7 mM | 6.9% |
|  | 2.8 mM | 6.3% |
|  | 11.2 mM | 5.9% |
| ×16 | 0 mM | 9.6% |
|  | 0.7 mM | 6.0% |
|  | 2.8 mM | 5.7% |
|  | 11.2 mM | 5.5% |

As shown in Table 6, in the method employing addition of a divalent metal salt after the thermal treatment, Et recovery was lower than 10%, failing to detect Et at high accuracy. Thus, it was elucidated that the divalent metal salt must be co-present with AT III and Et before the thermal treatment.

Example 4

Investigation into Acid Treatment

A 0.5-EU/mL Et standard solution (0.22 mL) was added to a 50-Unit/mL AT III pharmaceutical preparation (0.2 mL), and the mixture was vigorously agitated for one minute by means of a test tube mixer. Subsequently, water (1.8 mL) was added thereto, and the mixture was vigorously agitated for one minute by means of a test tube mixer. Subsequently, an aliquot (0.1 mL) of the mixture was dispensed another container. A 50 mM or 5 mM aqueous solution of a divalent metal salt was added in a 1/10 amount (0.011 mL) thereto, and the mixture was vigorously agitated for one minute by means of a test tube mixer. Thereafter, 5N, 2N, 1N, 0.5N, or 0.1N HCl (0.011 mL) was added thereto, and the mixture was vigorously agitated for one minute by means of a test tube mixer. An aliquot (0.05 mL) thereof was dispensed to a microplate. Endospecy ES-50 M (0.05 mL) was added to the microplate, and the microplate was vigorously agitated for one minute by means of a well-reader. Thereafter, the change over time in absorbance was monitored at a measurement wavelength of 405 nm and a reference wavelength of 492 nm, while the microplate was heated at 37° C. for 30 minutes, whereby and then the Et recovery was calculated. Table 7 shows the results. In Table 7, the divalent metal salt concentration and hydrochloric acid concentration are those of the reaction mixtures during the acid treatment (estimated values). The dilution factor of the AT III pharmaceutical preparation employed in Example 4 was about 14.

TABLE 7

Results of Et detection in the case of acid treatment in the co-presence of a divalent metal salt

| Co-present divalent metal salt | HCl concentration | Et recovery |
| --- | --- | --- |
| 0.5 mM $ZnSO_4$ | 0.01N | 37.5% |
|  | 0.05N | 66.9% |
|  | 0.1N | 30.3% |
|  | 0.2N | 7.9% |
|  | 0.5N | 2.9% |
| 5 mM $Ca(CH_3COO)_2$ | 0.01N | 11.6% |
|  | 0.05N | 51.0% |
|  | 0.1N | 54.6% |
|  | 0.2N | 6.9% |
|  | 0.5N | 3.3% |
| 5 mM $CaCl_2$ | 0.01N | 14.0% |
|  | 0.05N | 51.8% |
|  | 0.1N | 50.2% |
|  | 0.2N | 4.8% |
|  | 0.5N | 2.9% |
| 5 mM $Mg(CH_3COO)_2$ | 0.01N | 9.7% |
|  | 0.05N | 54.9% |
|  | 0.1N | 69.0% |
|  | 0.2N | No Data |
|  | 0.5N | 4.0% |
| 5 mM $MgSO_4$ | 0.01N | 36.8% |
|  | 0.05N | 59.1% |
|  | 0.1N | 64.3% |
|  | 0.2N | 4.9% |
|  | 0.5N | 4.0% |
| 5 mM $MnSO_4$ | 0.01N | 34.8% |
|  | 0.05N | 48.2% |
|  | 0.1N | 48.7% |
|  | 0.2N | No Data |
|  | 0.5N | 2.9% |

As shown in Table 7, through the acid treatment in the co-presence of a divalent metal, Et could be detected, similar to the case of the thermal treatment. Particularly when the hydrochloric acid concentration is 0.01 N to 0.1 N, Et could be efficiently detected.

Example 5

Test Employing Pyrochrome (Et Assay Reagent for Chromogenic Assay)

A 0.4-EU/mL Et standard solution (0.1 mL) was added to a 50-Unit/mL AT III pharmaceutical preparation (0.1 mL), and the mixture was vigorously agitated for one minute by means of a test tube mixer. Subsequently, water (0.1 mL) was added thereto, and the resultant mixture was vigorously agitated for one minute by means of a test tube mixer. Subsequently, a 25 mM aqueous $CaCl_2$ solution (0.1 mL) was added thereto, and the resultant mixture was vigorously agitated for one minute by means of a test tube mixer. An aliquot (0.2 mL) of the mixture was dispensed to another container as a 4-fold diluted solution of AT III. To the remaining portion (0.2 mL) of the mixture, water (0.2 mL) was added, and the resultant mixture was vigorously agitated for one minute by means of a test tube mixer. An aliquot (0.2 mL) of the thus-obtained diluted mixture was dispensed to another container as an 8-fold diluted solution of AT III. The operation was repeated, to thereby prepare a 16-fold diluted solution and a 32-fold diluted solution of AT III, and each diluted solution was dispensed to another container. Each of the thus-obtained solutions was heated at 70° C. for 10 minutes by means of a heat block, and then cooled with ice immediately after completion of heating. Each solution was returned to room temperature, and an aliquot (0.05 mL) thereof was dispensed to a microplate. An Et assay reagent for chromogenic assay (Pyrochrome; product of Associates of Cape Cod, Inc.) (0.05 mL) was added to the microplate, and the microplate was vigorously agitated for one minute by means of a well-reader. Thereafter, the change over time in absorbance was monitored at a measurement wavelength of 405 nm and a reference wavelength of 492 nm, while the microplate was heated at 37° C. for 60 minutes, and then the Et recovery was calculated. Table 8 shows the results.

TABLE 8

Results of Et detection through chromogenic assay
(Pyrochrome)

| Dilution factor | Et recovery |
| --- | --- |
| ×4 | 93.9% |
| ×8 | 96.2% |
| ×16 | 104.5% |
| ×32 | 104.8% |

As shown in Table 8, even when Pyrochrome was used as an Et assay reagent for chromogenic assay instead of Endospecy ES-50 M, the Et recovery of about 100% could be attained independently of the dilution factor for the AT III pharmaceutical preparation, i.e. Et could be detected at high accuracy. Therefore, it was elucidated that, even when Pyrochrome was used as an Et assay reagent for chromogenic assay, Et co-present with AT III could be measured at high accuracy through carrying out the pre-treatment method of the present invention.

Example 6

Test Employing Pyrotell-T (Et Assay Reagent for Turbidimetric Assay)

A 0.4-EU/mL Et standard solution (0.1 mL) was added to a 50-Unit/mL AT III pharmaceutical preparation (0.1 mL), and the mixture was vigorously agitated for one minute by means of a test tube mixer. Subsequently, water (0.1 mL) was added thereto, and the resultant mixture was vigorously agitated for one minute by means of a test tube mixer. Subsequently, a 25 mM aqueous $CaCl_2$ solution (0.1 mL) was added thereto, and the resultant mixture was vigorously agitated for one minute by means of a test tube mixer. An aliquot (0.2 mL) of the mixture was dispensed to another container as a 4-fold diluted solution of AT III. To the remaining portion (0.2 mL) of the mixture, water (0.2 mL) was added, and the resultant mixture was vigorously agitated for one minute by means of a test tube mixer. An aliquot (0.2 mL) of the thus-obtained diluted mixture was dispensed to another container as an 8-fold diluted solution of AT III. The operation was repeated, to thereby prepare a 16-fold diluted solution and a 32-fold diluted solution of AT III, and each diluted solution was dispensed to another container. Each of the thus-obtained solutions was heated at 70° C. for 10 minutes by means of a heat block, and then cooled with ice immediately after completion of heating. Each solution was returned to room temperature, and an aliquot (0.1 mL) was dispensed to a microplate. An Et assay reagent for turbidimetric assay (Pyrotell (registered trademark)-T; product of Associates of Cape Cod, Inc.) (0.1 mL) was added to the microplate, and the microplate was vigorously agitated for one minute by means of a well-reader. Thereafter, the change over time in absorbance was monitored at a measurement wavelength of 405 nm and a reference wavelength of 660 nm, while the microplate was heated at 37° C. for 60 minutes, and then the Et recovery was calculated. Table 9 shows the results.

TABLE 9

Results of Et detection through turbidimetric assay
(Pyrotell-T)

| Dilution factor | Et recovery |
| --- | --- |
| ×4 | 99.0% |
| ×8 | 86.2% |
| ×16 | 80.1% |
| ×32 | 85.5% |

As shown in Table 9, even when Pyrotell-T was used as an Et assay reagent instead of Endospecy ES-50 M, Et recovery of about 100% could be attained independently of the dilution factor for the AT III pharmaceutical preparation, i.e. Et could be detected at high accuracy. Therefore, it was elucidated that, even when an Et assay reagent for turbidimetric assay was used as a *limulus* reagent, Et co-present with AT III could be measured at high accuracy through carrying out the pre-treatment method of the present invention.

Example 7

Test Employing Pyrotell Multi-Test (Et Assay Reagent for Gel-Clot Assay)

A 0.24-EU/mL Et standard solution (0.1 mL) was added to a 50-Unit/mL AT III pharmaceutical preparation (0.1 mL), and the mixture was vigorously agitated for one minute by means of a test tube mixer. Subsequently, water (0.1 mL) was added thereto, and the resultant mixture was vigorously agitated for one minute by means of a test tube mixer. Subsequently, a 25 mM aqueous $CaCl_2$ solution (0.1 mL) was added thereto, and the resultant mixture was vigorously agitated for one minute by means of a test tube mixer. An aliquot (0.2 mL) of the mixture was dispensed to another container as a 4-fold diluted solution of AT III. To the remaining portion (0.2 mL) of the mixture, water (0.2 mL) was added, and the resultant mixture was vigorously agitated for one minute by means of a test tube mixer. An aliquot (0.2 mL) of the thus-obtained diluted mixture was dispensed to another container as an 8-fold diluted solution of AT III. The operation was repeated, to thereby prepare a 16-fold diluted solution and a 32-fold diluted solution of AT III, and each diluted solution was dispensed to another container. Each of the thus-obtained solutions was heated at 70° C. for 10 minutes by means of a heat block, and then cooled with ice immediately after completion of heating. Each solution was returned to room temperature, and an aliquot (0.1 mL) was dispensed to a round-bottom test tube. An Et assay reagent for gel-clot assay (Pyrotell (registered trademark) multi-test; product of Associates of Cape Cod, Inc.) (0.1 mL) was added to the test tube, and the resultant mixture was vigorously agitated for one minute by means of a test tube mixer, followed by heating at 37° C. for one hour by means of a heat block. Thereafter, the test tube was slowly tilted, and formation of solid gel of the contents which gel did not flow out was checked. Table 10 shows the results.

TABLE 10

Results of Et detection through gel-clot assay
(Pyrotell multi-test)

| Dilution factor | Et concentration | Evaluation |
| --- | --- | --- |
| ×4 | 0.06 EU/mL | + (positive) |
| ×8 | 0.03 EU/mL | + (positive) |

TABLE 10-continued

Results of Et detection through gel-clot assay
(Pyrotell multi-test)

| Dilution factor | Et concentration | Evaluation |
|---|---|---|
| ×16 | 0.015 EU/mL | – (negative) |
| ×32 | 0.0075 EU/mL | – (negative) |

As shown in Table 10, gel-clot of the contents was observed in an AT III solution containing Et at a concentration of 0.03 EU/mL, which is the detection limit by Pyrotell multi-test, or higher. Therefore, it was elucidated that, even when an Et assay reagent for a gel-clot assay was used as a *limulus* reagent, Et co-present with AT III could be detected at high accuracy through carrying out the pre-treatment method of the present invention.

Example 8

Test Employing Parallel Line Assay (1)

A 1-EU/mL Et standard solution (0.11 mL) was added to a 50-Unit/mL AT III pharmaceutical preparation (0.475 mL), and the mixture was vigorously agitated for one minute by means of a test tube mixer. Subsequently, water (0.475 mL) was added thereto, and the resultant mixture was vigorously agitated for one minute by means of a test tube mixer. Subsequently, a 500 mM aqueous $MgSO_4$ solution (0.05 mL) was added thereto, and the resultant mixture was vigorously agitated for one minute by means of a test tube mixer. The thus-obtained solution was heated at 70° C. for 10 minutes by means of a heat block, and then cooled with ice immediately after completion of heating. The solution was returned to room temperature, and an aliquot (0.5 mL) was dispensed to another container as a twice diluted solution of AT III. To the remaining portion (0.5 mL) of the mixture, water (0.5 mL) was added, and the resultant mixture was vigorously agitated for one minute by means of a test tube mixer. An aliquot (0.5 mL) of the thus-obtained diluted mixture was dispensed to another container as a 4-fold diluted solution of AT III. The operation was repeated, to thereby prepare an 8-fold diluted solution, a 16-fold diluted solution, and a 32-fold diluted solution of AT III, and each diluted solution was dispensed to another container. Separately, water for the endotoxin test was used instead of an AT III pharmaceutical preparation to prepare and provide a similar dilution series without the pre-treatment of the present invention as control specimens. Each solution (0.05 mL) was dispensed to a microplate. Endospecy ES-50 M (0.05 mL) was added to the microplate, and the microplate was vigorously agitated for one minute by means of a well-reader. Thereafter, the change over time in absorbance was monitored at a measurement wavelength of 405 nm and a reference wavelength of 492 nm, while the microplate was heated at 37° C. for 30 minutes. Table 11 and FIG. 1 show the results.

TABLE 11

Results of test employing parallel line assay (1) Measurement results of Et test water as specimen

| Et concn. EU/mL | log value | M1 | M2 | M3 | Average (log value) |
|---|---|---|---|---|---|
| 0.00619 | −2.208 | 0.880 | 0.880 | 0.930 | −0.048 |
| 0.01238 | −1.907 | 1.540 | 1.600 | 1.540 | 0.193 |
| 0.02475 | −1.606 | 2.970 | 2.970 | 2.970 | 0.473 |
| 0.04950 | −1.305 | 6.170 | 5.230 | 5.280 | 0.744 |
| 0.09900 | −1.004 | 10.150 | 10.120 | 10.110 | 1.005 |

(2) Measurement results of AT III preparation as specimen

| Dilution ratio | | Absorbance change rate (mAbs/min) | | | |
|---|---|---|---|---|---|
| | log value | M1 | M2 | M3 | Average (log value) |
| 0.02675 | −1.573 | 1.020 | 1.020 | 1.020 | 0.009 |
| 0.05350 | −1.272 | 1.750 | 1.760 | 1.930 | 0.258 |
| 0.10700 | −0.971 | 3.360 | 3.280 | 3.230 | 0.517 |
| 0.21400 | −0.670 | 6.520 | 6.650 | 6.650 | 0.820 |
| 0.42800 | −0.369 | 12.090 | 13.320 | 12.670 | 1.103 |

* M1, M2, and M3: Measurement 1, 2, and 3

As shown in FIG. 1, the measured absorbance change rates of AT III-containing specimens were log-log plotted with respect to the dilution factors, and the measured absorbance change rates of control specimens (twice dilution series of endotoxin standard solution with water for endotoxin test) were log-log plotted with respect to endotoxin concentrations. The thus-plotted two lines were tested in terms of parallelism through a parallel line assay. The assay was performed through statistical analysis by use of software specialized to the parallel line assay (PL603; product of Seikagaku Corporation). As a result, regression linearity was established in each line, and parallelism was established between the two lines. Thus, the test results were satisfactory. The Et recovery, calculated by dividing the Et concentration (0.275 EU/mL) calculated through the parallel line assay by the Et concentration of the control (0.232 EU/mL), was 118.5%.

Example 9

Test Employing Parallel Line Assay (2)

A 1-EU/mL Et standard solution (0.1 mL) was added to a 50-Unit/mL AT III pharmaceutical preparation (0.8 mL), and the mixture was vigorously agitated for one minute by means of a test tube mixer. Subsequently, water (0.02 mL) was added thereto, and the resultant mixture was vigorously agitated for one minute by means of a test tube mixer. Subsequently, a 500 mM aqueous $MgSO_4$ solution (0.08 mL) was added thereto, and the resultant mixture was vigorously agitated for one minute by means of a test tube mixer. The thus-obtained solution was heated at 70° C. for 10 minutes by means of a heat block, and then cooled with ice immediately after completion of heating. The solution was returned to room temperature, and an aliquot (0.5 mL) was dispensed to another container as a 1.25-fold diluted solution of AT III. To the remaining portion (0.5 mL) of the mixture, 40 mM aqueous $MgSO_4$ (0.5 mL) was added, and the resultant mixture was vigorously agitated for one minute by means of a test tube mixer. An aliquot (0.5 mL) of the thus-obtained diluted mixture was dispensed to another container as a 2.5-fold diluted solution of AT III. The operation was repeated, to thereby prepare a 5-fold diluted solution, a 10-fold diluted solution, and a 20-fold diluted solution of AT III, and each diluted solution was dispensed to another container. Separately, water for the endotoxin test was used instead of an AT III pharmaceutical preparation to prepare and provide a similar dilution series without the pre-treatment of the present invention as control specimens. Each solution (0.05 mL) was dispensed to a microplate. Endospecy ES-50 M (0.05 mL) was added to the microplate, and the microplate was vigorously agitated for one minute by means of a well-reader. Thereafter, the change over time in absorbance was monitored at a measurement wavelength of 405 nm and a reference wavelength of 492 nm, while the microplate was heated at 37° C. for 30 minutes. Table 12 and FIG. 2 show the results.

TABLE 12

(1) Measurement results of Et test water as specimen

| Et concn. | | Absorbance change rate (mAbs/min) | | |
|---|---|---|---|---|
| EU/mL | log value | M1 | M2 | Average (log value) |
| 0.00625 | −2.204 | 0.890 | 0.950 | −0.036 |
| 0.01250 | −1.903 | 1.660 | 1.430 | 0.188 |
| 0.02500 | −1.602 | 3.270 | 3.190 | 0.509 |
| 0.05000 | −1.301 | 5.950 | 6.050 | 0.778 |
| 0.10000 | −1.000 | 11.460 | 11.710 | 1.064 |

(2) Measurement results of AT III preparation as specimen

| Dilution ratio | | Absorbance change rate (mAbs/min) | | |
|---|---|---|---|---|
| | log value | M1 | M2 | Average (log value) |
| 0.05000 | −1.301 | 0.930 | 0.910 | −0.036 |
| 0.10000 | −1.000 | 1.690 | 1.690 | 0.228 |
| 0.20000 | −0.699 | 3.040 | 2.960 | 0.477 |
| 0.40000 | −0.398 | 5.560 | 5.650 | 0.749 |
| 0.80000 | −0.097 | 10.600 | 10.970 | 1.033 |

* M1 and M2: Measurement 1 and 2

As shown in FIG. 2, the measured absorbance change rates of AT III-containing specimens were log-log plotted with respect to the dilution factors, and the measured absorbance change rates of control specimens (twice dilution series of endotoxin standard solution with water for endotoxin test) were log-log plotted with respect to endotoxin concentrations. The thus-plotted two lines were tested in terms of parallelism through a parallel line assay. The assay was performed through statistical analysis by use of software specialized to the parallel line assay (PL603; product of Seikagaku Corporation). As a result, regression linearity was established in each line, and parallelism was established between the two lines. Thus, the test results were satisfactory. The Et recovery, calculated by dividing the Et concentration (0.122 EU/mL) calculated through the parallel line assay by the Et concentration of the control (0.125 EU/mL), was 97.6%.

Example 10

Test Employing Parallel Line Assay (3)

A 20-EU/mL Et standard solution (2.5 µL) was added to a 50-Unit/mL AT III pharmaceutical preparation (472.5 µL), and the mixture was vigorously agitated for one minute by means of a test tube mixer. Subsequently, water (6.25 µL) was added thereto, and the resultant mixture was vigorously agitated for one minute by means of a test tube mixer. Subsequently, a 2M aqueous $MgSO_4$ solution (18.75 µL) was added thereto, and the resultant mixture was vigorously agitated for one minute by means of a test tube mixer. The thus-obtained solution was heated at 70° C. for 20 minutes by means of a heat block, and then cooled with ice immediately after completion of heating. The solution was returned to room temperature, and an aliquot (250 µL) was dispensed to another container as a 1.06-fold diluted solution of AT III. To the remaining portion (250 µL) of the mixture, water (250 µL) was added, and the resultant mixture was vigorously agitated for one minute by means of a test tube mixer. An aliquot (250 µL) of the thus-obtained diluted mixture was dispensed to another container as a 2.12-fold diluted solution of AT III. The operation was repeated, to thereby prepare a 4.23-fold diluted solution, an 8.47-fold diluted solution, and a 16.93-fold diluted solution of AT III, and each diluted solution was dispensed to another container. Separately, water for the endotoxin test was used instead of an AT III pharmaceutical preparation to prepare and provide a similar dilution series without the pre-treatment of the present invention as control specimens. Each solution (50 µL) was dispensed to a microplate. Endospecy ES-50 M (50 µL) was added to the microplate, and the microplate was vigorously agitated for one minute by means of a well-reader. Thereafter, the change over time in absorbance was monitored at a measurement wavelength of 405 nm and a reference wavelength of 492 nm, while the microplate was heated at 37° C. for 30 minutes. Table 13 and FIG. 3 show the results.

TABLE 13

(1) Measurement results of Et test water as specimen

| Et concn. | | Absorbance change rate (mAbs/min) | | |
|---|---|---|---|---|
| EU/mL | log value | M1 | M2 | Average (log value) |
| 0.00625 | −2.204 | 0.860 | 0.880 | −0.061 |
| 0.01250 | −1.903 | 1.460 | 1.420 | 0.158 |
| 0.02500 | −1.602 | 2.600 | 2.520 | 0.408 |
| 0.05000 | −1.301 | 5.050 | 4.970 | 0.700 |
| 0.10000 | −1.000 | 9.400 | 9.580 | 0.977 |

(2) Measurement results of AT III preparation as specimen

| Dilution ratio | | Absorbance change rate (mAbs/min) | | |
|---|---|---|---|---|
| | log value | M1 | M2 | Average (log value) |
| 0.05906 | −1.229 | 0.920 | 0.930 | −0.034 |
| 0.11813 | −0.928 | 1.510 | 1.620 | 0.194 |
| 0.23625 | −0.627 | 2.870 | 3.210 | 0.482 |
| 0.47250 | −0.326 | 4.580 | 5.540 | 0.702 |
| 0.94500 | −0.025 | 7.960 | 8.640 | 0.919 |

* M1 and M2: Measurement 1 and 2

As shown in FIG. 3, the measured absorbance change rates of AT III-containing specimens were log-log plotted with respect to the dilution factors, and the measured absorbance change rates of control specimens (twice dilution series of endotoxin standard solution with water for endotoxin test) were log-log plotted with respect to endotoxin concentrations. The thus-plotted two lines were tested in terms of parallelism through a parallel line assay. The assay was performed through statistical analysis by use of software specialized to the parallel line assay (PL603; product of Seikagaku Corporation). As a result, regression linearity was established in each line, and parallelism was established between the two lines. Thus, the test results were satisfactory. The Et recovery, calculated by dividing the Et concentration (0.111 EU/mL) calculated through the parallel line assay by the Et concentration of the control (0.106 EU/mL), was 104.7%.

Thus, as shown in Examples 8 to 10, through performing the pre-treatment of the present invention, Et co-present with AT III can be measured at high accuracy, even in the test according to the parallel line assay described in the biological pharmaceutical preparation standards.

INDUSTRIAL APPLICABILITY

According to the present invention, by performing a pre-treatment of AT III to be subjected to *limulus* test, reaction interference observed when AT III is subjected to *limulus* test can be reduced, and thus, *limulus* test of AT III can be carried out at high accuracy. Also, according to the present invention, *limulus* test of AT III is expected to be carried out in a simple and speedy manner at low cost.

The invention claimed is:

1. A pre-treatment method for antithrombin III to be subjected to *limulus* test, the method comprising subjecting antithrombin III to a protein inactivation treatment, wherein the protein inactivation treatment is conducted in the co-presence of the pre-treatment agent which contains a divalent metal salt and wherein the protein inactivation treatment is not an alkali treatment, wherein antithrombin III is an injection pharmaceutical preparation of antithrombin III, and wherein a target substance of the *limulus* test is endotoxin.

2. The pre-treatment method according to claim 1, wherein the protein inactivation treatment is a thermal treatment or an acid treatment.

3. The pre-treatment method according to claim 2, wherein the thermal treatment is performed at a temperature higher than 50° C.

4. The pre-treatment method according to claim 2, wherein the acid employed in the acid treatment is hydrochloric acid.

5. A method for measuring endotoxin contained in an injection pharmaceutical preparation of antithrombin III, the method comprising preliminarily treating the injection pharmaceutical preparation of antithrombin III through the pre-treatment method according to claim 1, and subjecting the preliminarily treated injection pharmaceutical preparation of antithrombin III to *limulus* test.

6. A method for producing an injection pharmaceutical preparation of antithrombin III, the method comprising measuring endotoxin in the injection pharmaceutical preparation of antithrombin III through the method according to claim 5.

* * * * *

UNITED STATES PATENT AND TRADEMARK OFFICE
CERTIFICATE OF CORRECTION

PATENT NO. : 10,132,812 B2
APPLICATION NO. : 14/758269
DATED : November 20, 2018
INVENTOR(S) : Maki Aizawa, Toshio Oda and Jun Aketagawa It is certified that error appears in the above-identified patent and that said Letters Patent is hereby corrected as shown below:

In the Specification

At Column 1, Line 28:
Delete "BG: (1→43)-β-D-glucan" and insert --BG: (1→3)-β-D-glucan--

At Column 8, Line 36:
Delete "Walkerrsville" and insert --Walkersville--

Signed and Sealed this
Nineteenth Day of February, 2019

Andrei Iancu
*Director of the United States Patent and Trademark Office*